United States Patent
Lee et al.

(10) Patent No.: US 10,905,399 B2
(45) Date of Patent: Feb. 2, 2021

(54) ULTRASOUND APPARATUS AND METHOD OF OBTAINING INFORMATION FROM CONTRAST IMAGE

(71) Applicant: SAMSUNG MEDISON CO., LTD., Hongcheon-gun (KR)

(72) Inventors: Jin-yong Lee, Hongcheon-gun (KR); Jong-sik Kim, Hongcheon-gun (KR); Sung-wook Park, Hongcheon-gun (KR)

(73) Assignee: SAMSUNG MEDISON CO., LTD., Gangwon-do (KR)

( * ) Notice: Subject to any disclaimer, the term of this patent is extended or adjusted under 35 U.S.C. 154(b) by 601 days.

(21) Appl. No.: 15/082,220

(22) Filed: Mar. 28, 2016

(65) Prior Publication Data
US 2017/0071571 A1 Mar. 16, 2017

(30) Foreign Application Priority Data
Sep. 15, 2015 (KR) .......... 10-2015-0130611

(51) Int. Cl.
*A61B 8/00* (2006.01)
*A61B 8/08* (2006.01)
*A61B 8/14* (2006.01)

(52) U.S. Cl.
CPC .......... *A61B 8/465* (2013.01); *A61B 8/085* (2013.01); *A61B 8/14* (2013.01); *A61B 8/4444* (2013.01);
(Continued)

(58) Field of Classification Search
CPC ......... A61B 8/469; A61B 8/14; A61B 8/4444; A61B 8/465; A61B 8/481; A61B 8/483;
(Continued)

(56) References Cited

U.S. PATENT DOCUMENTS

| 6,193,660 B1 * | 2/2001 | Jackson .......... A61B 8/00 600/443 |
| 8,460,192 B2 | 6/2013 | Yoshiara et al. |

(Continued)

FOREIGN PATENT DOCUMENTS

| JP | 2001-269341 A | 10/2001 |
| JP | 2005-137674 A | 6/2005 |

(Continued)

OTHER PUBLICATIONS

Liu et. al., "Contrast-enhanced Ultrasound imaging—Sate of the Art", J. Med. Ultrasound 2005; 13(3) 109-126.*
(Continued)

*Primary Examiner* — Pascal M Bui Pho
*Assistant Examiner* — Yi-Shan Yang
(74) *Attorney, Agent, or Firm* — Sughrue Mion, PLLC

(57) ABSTRACT

Provided is an ultrasound diagnosis apparatus including: an image processor configured to generate, as an amount of a contrast agent introduced into a target tissue of an object changes, a plurality of ultrasound images showing different sizes of regions in a target tissue region representing a tissue into which the contrast agent has been introduced; a display configured to display a first ultrasound image from among the plurality of ultrasound images; a user input unit configured to receive a user input for setting a region of interest (ROI) in the displayed first ultrasound image; and a controller configured to determine, based on the set ROI, the regions in the plurality of ultrasound images representing the tissue into which the contrast agent has been introduced and determine the region of the target tissue based on the determined regions.

16 Claims, 12 Drawing Sheets

(52) U.S. Cl.
CPC .............. *A61B 8/466* (2013.01); *A61B 8/469* (2013.01); *A61B 8/481* (2013.01); *A61B 8/483* (2013.01); *A61B 8/486* (2013.01); *A61B 8/488* (2013.01); *A61B 8/5207* (2013.01); *A61B 8/5292* (2013.01); *A61B 8/54* (2013.01); *A61B 8/565* (2013.01)

(58) Field of Classification Search
CPC ....... A61B 8/486; A61B 8/488; A61B 8/5207; A61B 8/54; A61B 8/565; A61B 8/085
See application file for complete search history.

(56) References Cited

U.S. PATENT DOCUMENTS

| | | | | |
|---|---|---|---|---|
| 2005/0075567 | A1* | 4/2005 | Skyba | A61B 8/481 600/443 |
| 2005/0148861 | A1* | 7/2005 | Ramanathan | G06F 19/321 600/410 |
| 2009/0030322 | A1* | 1/2009 | Fujiwara | A61B 8/06 600/458 |
| 2010/0081938 | A1* | 4/2010 | Kato | A61B 8/06 600/458 |
| 2010/0094133 | A1* | 4/2010 | Yoshiara | A61B 8/08 600/453 |
| 2011/0054295 | A1* | 3/2011 | Masumoto | A61B 5/055 600/407 |
| 2013/0116565 | A1* | 5/2013 | Miyama | A61B 8/481 600/443 |
| 2013/0137984 | A1 | 5/2013 | Takagi et al. | |
| 2014/0350439 | A1 | 11/2014 | Zur et al. | |
| 2015/0087979 | A1 | 3/2015 | Zhang et al. | |

FOREIGN PATENT DOCUMENTS

| | | |
|---|---|---|
| JP | 4369206 B2 | 11/2009 |
| JP | 2010-94220 A | 4/2010 |
| JP | 2011-115457 A | 6/2011 |

OTHER PUBLICATIONS

Rueckert et al., "Nonrigid Registration Using Free-Form Deformations: Application to Breast MR Images". IEEE Transaction on Medical Imaging. vol. 18, No. 8, 1999, 712-721.*
Communication dated Feb. 15, 2017, from the European Patent Office in counterpart European Application No. 16152158.8.

* cited by examiner

ULTRASOUND APPARATUS AND METHOD OF OBTAINING INFORMATION FROM CONTRAST IMAGE

CROSS-REFERENCE TO RELATED APPLICATION

This application claims the benefit of Korean Patent Application No. 10-2015-0130611, filed on Sep. 15, 2015, in the Korean Intellectual Property Office, the disclosure of which is incorporated herein in its entirety by reference.

BACKGROUND

1. Field

The present disclosure relates to methods and apparatuses for determining a target tissue region in a contrast image and providing information about whether a target tissue includes a lesion based on the determined target tissue region.

2. Description of the Related Art

Ultrasound diagnosis apparatuses transmit ultrasound signals generated by transducers of a probe to an object and receive echo signals reflected from the object, thereby obtaining at least one image of an internal part of the object (e.g., soft tissues or blood flow). In particular, ultrasound diagnosis apparatuses are used for medical purposes including observing an inner area of an object, detecting foreign substances, and assessing injuries. Such ultrasound diagnosis apparatuses provide high stability, display images in real time, and are safe due to there being no radiation exposure, compared to X-ray apparatuses. Therefore, an ultrasound diagnosis apparatus is widely used together with other types of image diagnosis apparatuses including a computed tomography (CT) apparatus, a magnetic resonance imaging (MRI) apparatus, and the like.

SUMMARY

Provided are methods and apparatuses for determining a target tissue region in a contrast image.

Additional aspects will be set forth in part in the description which follows and, in part, will be apparent from the description, or may be learned by practice of the presented exemplary embodiments.

According to an aspect of an exemplary embodiment, an ultrasound diagnosis apparatus includes: an image processor configured to generate, as an amount of a contrast agent introduced into a target tissue of an object changes, a plurality of ultrasound images showing different sizes of regions in a target tissue region, representing a tissue into which the contrast agent has been introduced; a display configured to display a first ultrasound image from among the plurality of ultrasound images; a user input unit configured to receive a user input for setting a region of interest (ROI) in the displayed first ultrasound image; and a controller configured to determine, based on the set ROI, the regions in the plurality of ultrasound images representing the tissue into which the contrast agent has been introduced and determine the region of the target tissue based on the determined regions.

The controller may calculate an average of brightness values of the determined region of the target tissue with respect to time.

The controller may determine the regions representing the tissue into which the contrast agent has been introduced, based on at least one of a position and a brightness value of the set ROI.

The controller may determine the regions representing the tissue into which the contrast agent has been introduced by expanding the ROI to a region having a brightness value whose difference from a brightness value of the ROI is less than or equal to a preset value, from among regions in a second ultrasound image subsequent to the first ultrasound image among the plurality of ultrasound images.

The display may display the second ultrasound image subsequently to the first ultrasound image and shows expansion of the ROI as a size of a region representing the tissue into which the contrast agent has been introduced changes by displaying the expanded ROI on the displayed second ultrasound image.

The controller may determine the region having a maximum size from among the regions in the plurality of ultrasound images representing the tissue into which the contrast agent has been introduced by taking into account a shape of the ROI set in the first ultrasound image.

The display may display an ultrasound image showing the region having a maximum size from among the plurality of ultrasound images and display the region of the target tissue on the displayed ultrasound image.

The user input unit may receive a user input for adjusting the displayed region of the target tissue, and the controller may recalculate, based on the adjusted region of the target tissue, an average of brightness values of the adjusted region of the target tissue with respect to time.

The display may display the plurality of ultrasound images sequentially and display the determined region of the target tissue on the displayed plurality of ultrasound images.

The display may display a graph representing the calculated average of brightness values of the region of the target tissue with respect to time.

According to an aspect of another exemplary embodiment, a method of acquiring information based on a contrast image includes: generating, as an amount of a contrast agent introduced into a target tissue of an object changes, a plurality of ultrasound images showing different sizes of regions in a region of the target tissue, representing a tissue into which the contrast agent has been introduced; displaying a first ultrasound image from among the plurality of ultrasound images; receiving a user input for setting an ROI in the displayed first ultrasound image; determining, based on the set ROI, the regions in the plurality of ultrasound images representing the tissue into which the contrast agent has been introduced; and determining the region of the target tissue based on the determined regions.

The method may further include calculating an average of brightness values of the determined region of the target tissue with respect to time.

The determining of the regions in the plurality of ultrasound images representing the tissue into which the contrast agent has been introduced based on the set ROI may include determining the regions representing the tissue into which the contrast agent has been introduced, based on at least one of a position and a brightness value of the set ROI.

The determining of the regions in the plurality of ultrasound images representing the tissue into which the contrast agent has been introduced based on the set ROI may include determining the regions representing the tissue into which the contrast agent has been introduced by expanding the ROI to a region having a brightness value whose difference from a brightness value of the ROI is less than or equal to a preset value, from among regions in a second ultrasound image subsequent to the first ultrasound image among the plurality of ultrasound images.

The method may further include: displaying the second ultrasound image subsequently to the first ultrasound image; and showing expansion of the ROI as a size of a region representing the tissue into which the contrast agent has been introduced changes by displaying the expanded ROI on the displayed second ultrasound image.

The determining of the regions in the plurality of ultrasound images representing the tissue into which the contrast agent has been introduced based on the set ROI may include determining the region having a maximum size from among the regions in the plurality of ultrasound images representing the tissue into which the contrast agent has been introduced by taking into account a shape of the ROI set in the first ultrasound image.

The method may further include: displaying an ultrasound image showing the region having a maximum size from among the plurality of ultrasound images; and displaying the region of the target tissue on the displayed ultrasound image.

The method may further include: receiving a user input for adjusting the displayed region of the target tissue; and recalculating, based on the adjusted region of the target tissue, an average of brightness values of the adjusted region of the target tissue with respect to time.

The method may further include: displaying the plurality of ultrasound images sequentially; and displaying the determined region of the target tissue on the displayed plurality of ultrasound images.

The method may further include displaying a graph representing the calculated average of brightness values of the region of the target tissue with respect to time.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1A:
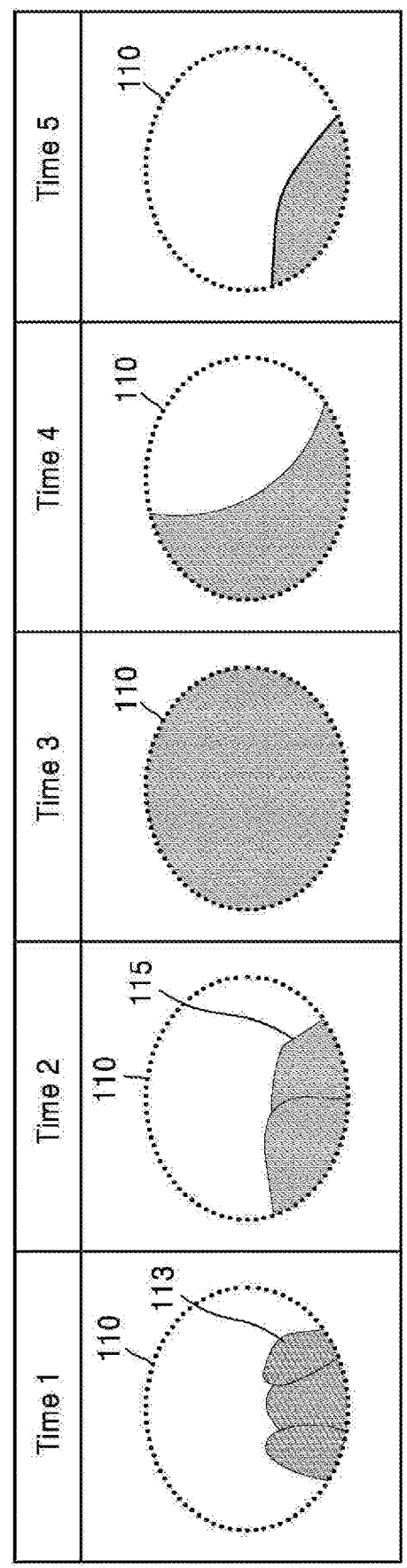
FIGS. 1A through 1C illustrate an example in which an ultrasound diagnosis apparatus calculates a variation in brightness values of a target tissue region with respect to time from an ultrasound image, according to an exemplary embodiment.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used herein have to be defined based on the meaning of the terms together with the description throughout the specification.

When a part "includes" or "comprises" an element, unless there is a particular description contrary thereto, the part can further include other elements, not excluding the other elements. In addition, terms such as " . . . unit", " . . . module", or the like refer to units that perform at least one function or operation, and the units may be implemented as hardware or software or as a combination of hardware and software.

Reference will now be made in detail to embodiments, examples of which are illustrated in the accompanying drawings. In this regard, the present embodiments may have different forms and should not be construed as being limited to the descriptions set forth herein. Exemplary embodiments will now be described more fully hereinafter with reference to the accompanying drawings so that they may be easily implemented by one of ordinary skill in the art. However, the present embodiments may have different forms and should not be construed as being limited to the descriptions set forth herein. In addition, parts not related to the present inventive concept are omitted to clarify the description of exemplary embodiments. Like reference numerals refer to like elements throughout. Expressions such as "at least one of," when preceding a list of elements, modify the entire list of elements and do not modify the individual elements of the list.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

Throughout the specification, a "user" may be, but is not limited to, a medical expert, for example, a medical doctor, a nurse, a medical laboratory technologist, or a medical imaging expert, or a technician who repairs medical apparatuses.

Throughout the specification, a "brightness value" of a target tissue may be an "intensity" of an ultrasound echo signals reflected from the target tissue.

Hereinafter, exemplary embodiments will be described in detail with reference to the accompanying drawings.

Figure 1B:
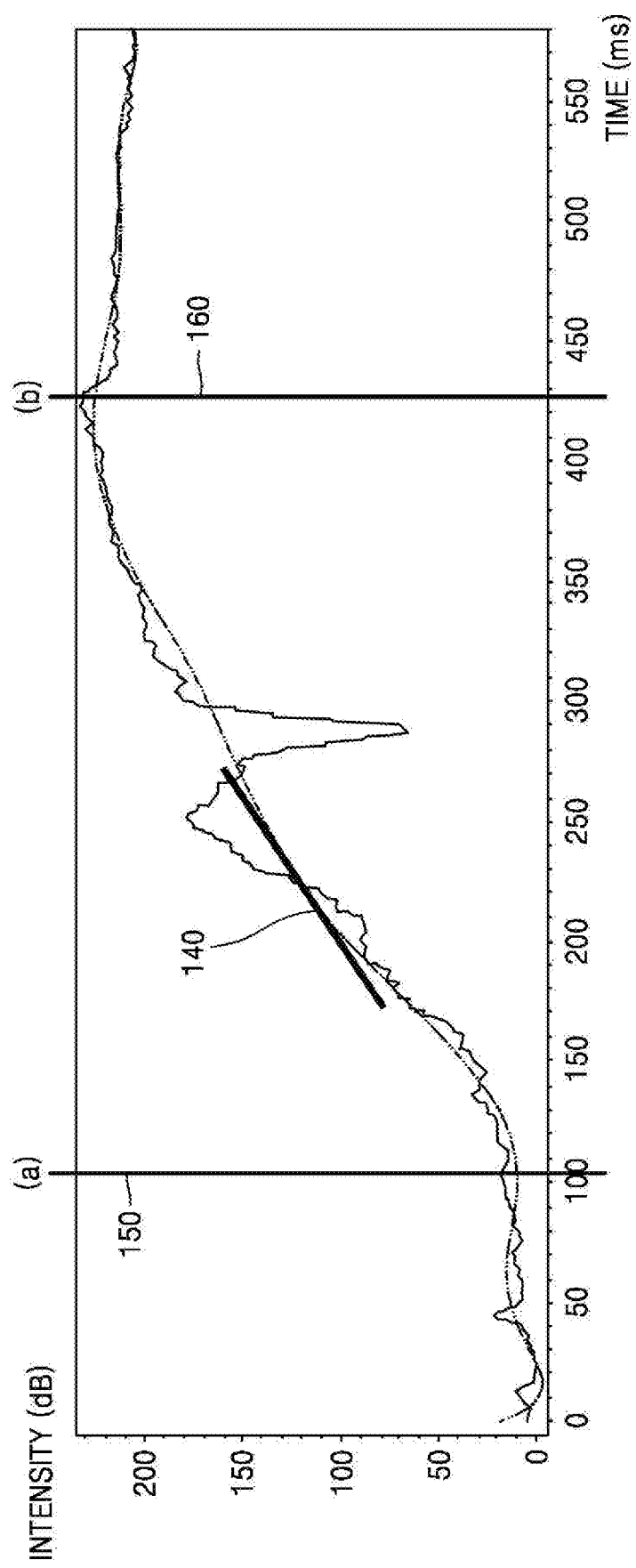
Figure 1C:
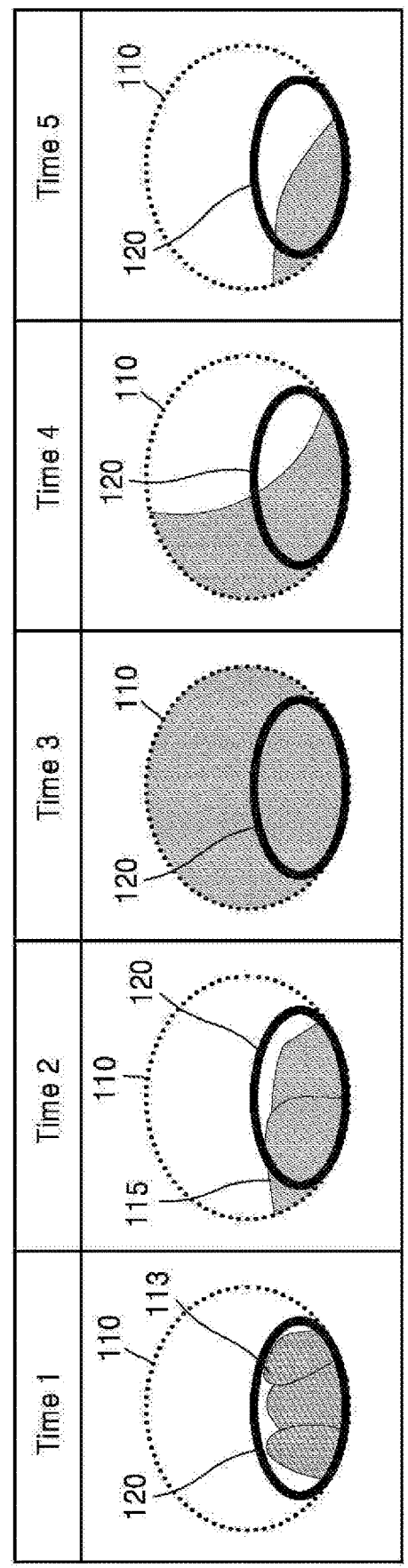
Figure 8:
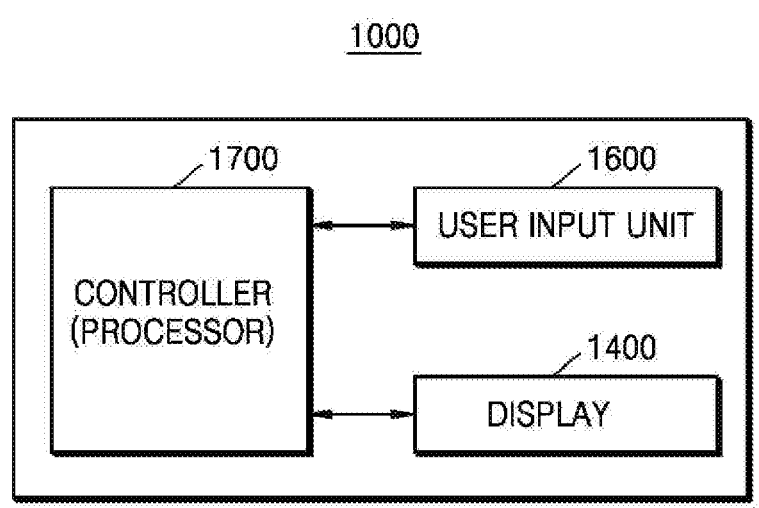
FIG. 8 is a block diagram of an ultrasound diagnosis apparatus according to an exemplary embodiment.
Figure 9:
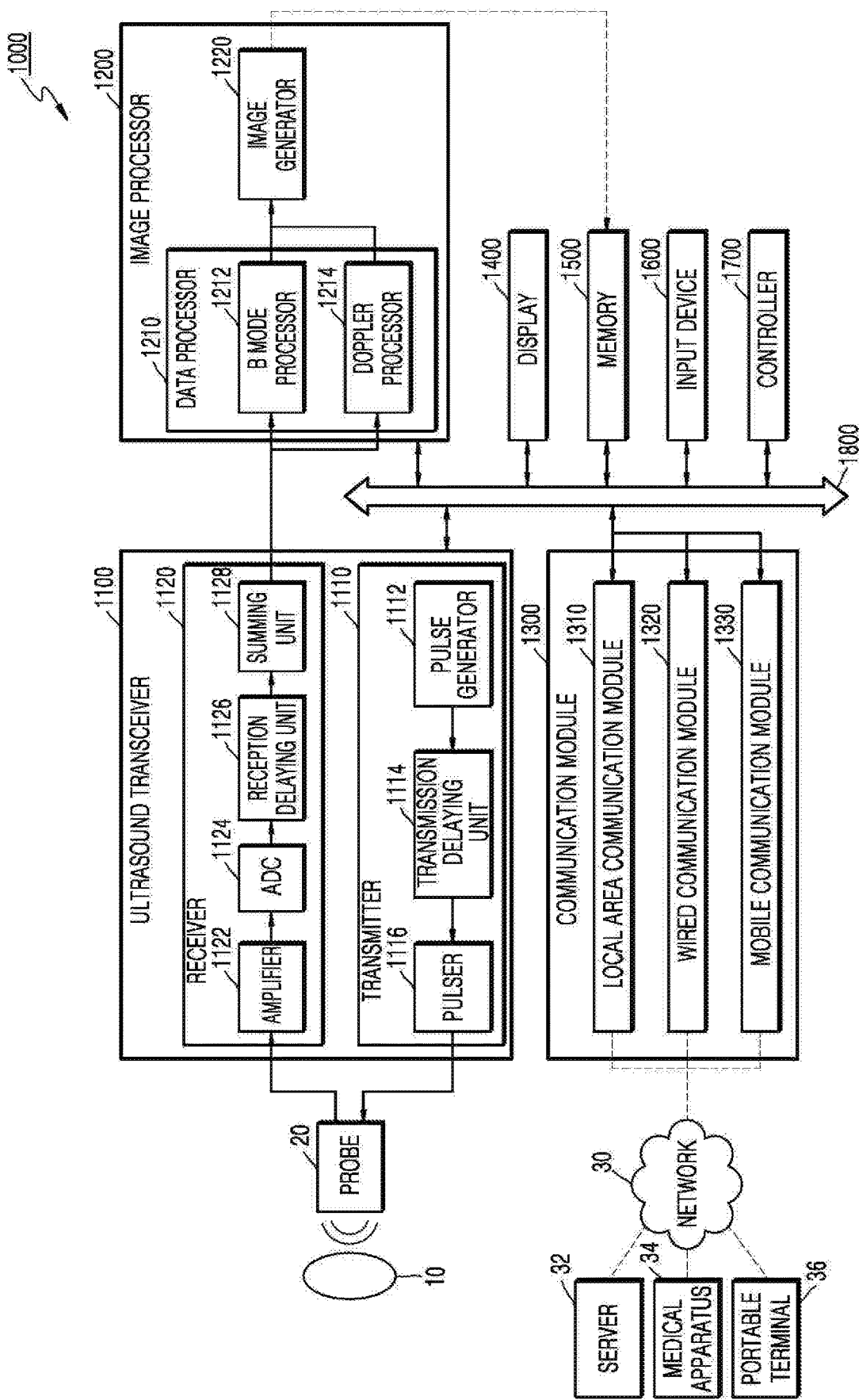
FIG. 9 is a block diagram of an ultrasound diagnosis apparatus according to another exemplary embodiment.

FIGS. 1A through 1C illustrate an example in which an ultrasound diagnosis apparatus 1000 of FIG. 8 or 9 calculates a variation in brightness values of a target tissue region 110 with respect to time from an ultrasound image, according to an exemplary embodiment.

Referring to FIG. 1A, after a contrast agent is introduced, the ultrasound diagnosis apparatus 1000 may display an ultrasound image of target tissue with respect to time. According to an exemplary embodiment, the ultrasound image may also be referred to as a "contrast image". Furthermore, examples of the ultrasound image may include not only a 2D ultrasound image but also a 3D ultrasound image.

An intensity of an ultrasound signal reflected from a contrast agent may be greater than an intensity of a signal reflected from ordinary body tissue. Thus, as a contrast agent is introduced into a target tissue of an object, a portion of a target tissue region into which the contrast agent has been introduced may appear distinctly brighter in an ultrasound image than the rest of the target tissue region.

In general, a contrast agent flows into a tissue in the human body along with blood flow. Thus, as the contrast agent is introduced into a target tissue of an object, an ultrasound image shows gradual expansion of a bright region from a region adjacent to a blood vessel supplying a flow of blood to the target tissue to the entire target tissue.

An ultrasound image of the target tissue region 110 shown at time 1 of FIG. 1A may be an ultrasound image of the target tissue captured by the ultrasound diagnosis apparatus 1000 after a contrast agent is introduced into the target tissue. On the ultrasound image of the target tissue region 110 shown at time 1, only a portion 113 of the target tissue region 110 into which the contrast agent has been introduced may appear brighter than the rest of the target tissue region 110.

When the ultrasound image is a 2D ultrasound image, the target tissue region 110 may be a region in the 2D ultrasound image. When the ultrasound image is a 3D ultrasound image, the target tissue region 110 may be a portion of a 3D volume in the 3D ultrasound image.

As the contrast agent is further introduced into the target tissue, a portion that appears bright in the target tissue region 110 may also expand due to expansion of a region reflected by the contrast agent. Thus, when time 2 has elapsed, a portion 115 wider than the portion 113 may appear bright in the target tissue region 110. Furthermore, when time 3 has elapsed, the entire target tissue region 110 may appear bright.

Furthermore, as time elapses, the contrast agent introduced into the target tissue may be passed out of the target tissue, and accordingly, a region reflected by the contrast agent may be reduced. Thus, when time 4 has elapsed, a portion that appears bright in the target tissue region 110 may be reduced. Furthermore, when time 5 has elapsed, a region that appears bright in the target tissue region 110 may be further reduced.

FIG. 1B is a graph of an average of brightness values (hereinafter referred to as an "average brightness value") of the target tissue region 110 in an ultrasound image with respect to time.

As shown in the graph of FIG. 1B, when a target tissue is a tissue having a lesion such as cancerous tissue, since a contrast agent flows quickly into the target tissue, an average brightness value for the target tissue region 110 increases rapidly over time. On the other hand, when the target tissue is ordinary tissue having no lesion, an average brightness value for the target tissue region 110 gradually increases over time.

Thus, the user may determine whether the target tissue region 110 is a region having a lesion based on at least one of a slope 140 of a curve representing average brightness values, a time 150 when a brightness value begins to increase, a time 160 when a brightness value reaches a maximum, and a maximum average brightness value.

The ultrasound diagnosis apparatus 1000 may determine tissue characteristics when the contrast agent is introduced into the target tissue region 110. Depending on the type of a lesion or according to an exemplary embodiment, the ultrasound diagnosis apparatus 1000 may determine tissue characteristics when the contrast agent leaves the target tissue region 110.

In addition, before calculating an average brightness value for the target tissue region 110, the ultrasound diagnosis apparatus 1000 may determine the target tissue region 110 in an ultrasound image.

Referring to FIG. 1C, the ultrasound diagnosis apparatus 1000 may receive a user input for setting a virtual target tissue region 120.

For example, after a contrast agent is introduced into a target tissue, the ultrasound diagnosis apparatus 1000 may display an ultrasound image captured at time 1 and receive a user input for setting the virtual target tissue region 120 in the displayed ultrasound image. In this case, since only a portion 113 of the actual target tissue region 110 is shown in the ultrasound image, the user may set the virtual target tissue region 120 to include only the portion 113 shown in the ultrasound image.

When a user input for setting the virtual target tissue region 120 is received, the ultrasound diagnosis apparatus 1000 may calculate an average brightness value for the virtual target tissue region 120 with respect to time. In this case, since the virtual target tissue region 120 is a part of the actual target tissue region 110, an average brightness value of the virtual target tissue region 120 may be different from that of the actual target tissue region 110. For example, a rate at which an average brightness value of the virtual target tissue region 120 increases over time may be similar to a rate at which an average brightness value of ordinary tissue increases over time. Thus, despite the tissue containing a lesion, the actual target tissue region 110 may be determined to be ordinary tissue.

Figure 2:
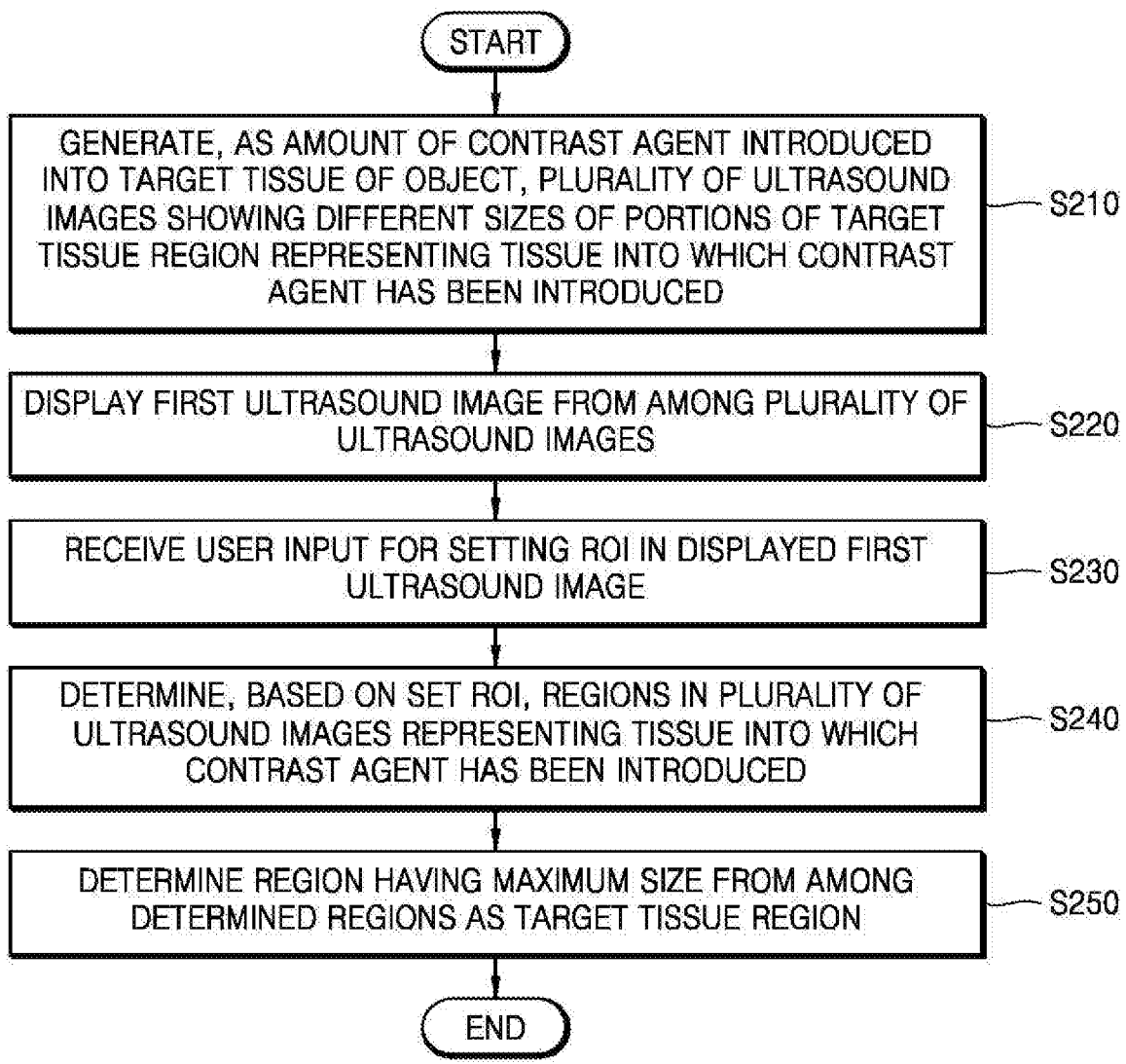
FIG. 2 is a flowchart of a method of determining a target tissue region based on a region of interest (ROI) via an ultrasound diagnosis apparatus, according to an exemplary embodiment.

FIG. 2 is a flowchart of a method of determining a target tissue region based on a region of interest (ROI) via the ultrasound diagnosis apparatus 1000, according to an exemplary embodiment.

As the amount of a contrast agent introduced into a target tissue of an object changes, the ultrasound diagnosis apparatus 1000 may generate a plurality of ultrasound images showing different sizes of portions of a target tissue region representing tissue into which the contrast agent has been introduced (S210).

After a contrast agent is introduced into an object, the ultrasound diagnosis apparatus 1000 may capture an image of a target tissue region of an object according to a user input. As the amount of the contrast agent introduced into the target tissue of the object changes, the ultrasound diagnosis apparatus 1000 may generate a plurality of ultrasound images showing different sizes of portions of a target tissue region representing a tissue into which the contrast agent has been introduced. A portion representing a tissue into which the contrast agent has been introduced may have a brightness value greater than or equal to a reference value.

The ultrasound diagnosis apparatus 1000 may display a first ultrasound image from among the plurality of ultrasound images (S220).

The ultrasound diagnosis apparatus 1000 may determine an ultrasound image captured when the contrast agent begins to be introduced into the target tissue as the first ultrasound image and display the determined first ultrasound image. Furthermore, the ultrasound diagnosis apparatus 1000 may display a plurality of ultrasound images and, when a user input for selecting one of the displayed plurality of ultrasound images is received, display the selected ultrasound image.

The ultrasound diagnosis apparatus 1000 may receive a user input for setting an ROI in the displayed first ultrasound image (S230).

The ultrasound diagnosis apparatus 1000 may receive a user input for setting an ROI in the first ultrasound image. For example, the ultrasound diagnosis apparatus 1000 may receive a touch input for setting an ROI in the first ultrasound image displayed on a touch screen. As another example, the ultrasound diagnosis apparatus 1000 may receive a user input for setting an ROI by moving a trackball in a control panel.

The ultrasound diagnosis apparatus 1000 may determine, based on the set ROI, regions in the plurality of ultrasound images representing a tissue into which the contrast agent has been introduced (S240).

The ultrasound diagnosis apparatus 1000 may determine regions representing the tissue into which the contrast agent has been introduced, based on at least one of a position and a brightness value of the set ROI. For example, the ultrasound diagnosis apparatus 1000 may determine the regions representing the tissue into which the contrast agent has been introduced by expanding the ROI to a region having a brightness value whose difference from the brightness value of the ROI is less than or equal to a preset value, from among regions in a second ultrasound image subsequent to the first ultrasound image.

Furthermore, by taking into account a shape of the ROI set in the first ultrasound image, the ultrasound diagnosis apparatus 1000 may determine a region having a maximum size from among the regions in the plurality of ultrasound images representing the tissue into which the contrast agent has been introduced.

The ultrasound diagnosis apparatus 1000 may determine as a target tissue region the region having a maximum size from among the determined regions (S250).

The ultrasound diagnosis apparatus 1000 may determine as a target tissue region a region having a maximum size from among regions representing a tissue into which a contrast agent has been introduced and respectively determined in the corresponding plurality of ultrasound images.

Furthermore, according to an exemplary embodiment, the ultrasound diagnosis apparatus 1000 may determine as a target tissue region a region having a second maximum size from among regions representing a tissue into which a contrast agent has been introduced and respectively determined in the corresponding plurality of ultrasound images.

Furthermore, the ultrasound diagnosis apparatus 1000 may calculate an average of brightness values of the determined target tissue region with respect to time.

Furthermore, after displaying of the first ultrasound image and setting of the ROI in the first ultrasound image, the ultrasound diagnosis apparatus 1000 may display the second ultrasound image and display an expanded ROI on the displayed second ultrasound image. Thus, the ultrasound diagnosis apparatus 1000 may show expansion of the ROI as a size of a region representing a tissue into which the contrast agent has been introduced changes.

Furthermore, the ultrasound diagnosis apparatus 1000 may display an ultrasound image showing a region having a maximum size from among a plurality of ultrasound images and display a target tissue region on the displayed ultrasound image.

Furthermore, the ultrasound diagnosis apparatus 1000 may receive a user input for adjusting the displayed target tissue region and recalculate brightness values of the adjusted target tissue region with respect to time based on the adjusted target tissue region.

Furthermore, the ultrasound diagnosis apparatus 1000 may display a plurality of ultrasound images sequentially and display the determined target tissue region on the displayed plurality of ultrasound images.

Furthermore, the ultrasound diagnosis apparatus 1000 may display a graph representing a calculated average brightness value of the target tissue region with respect to time.

Figure 3A:
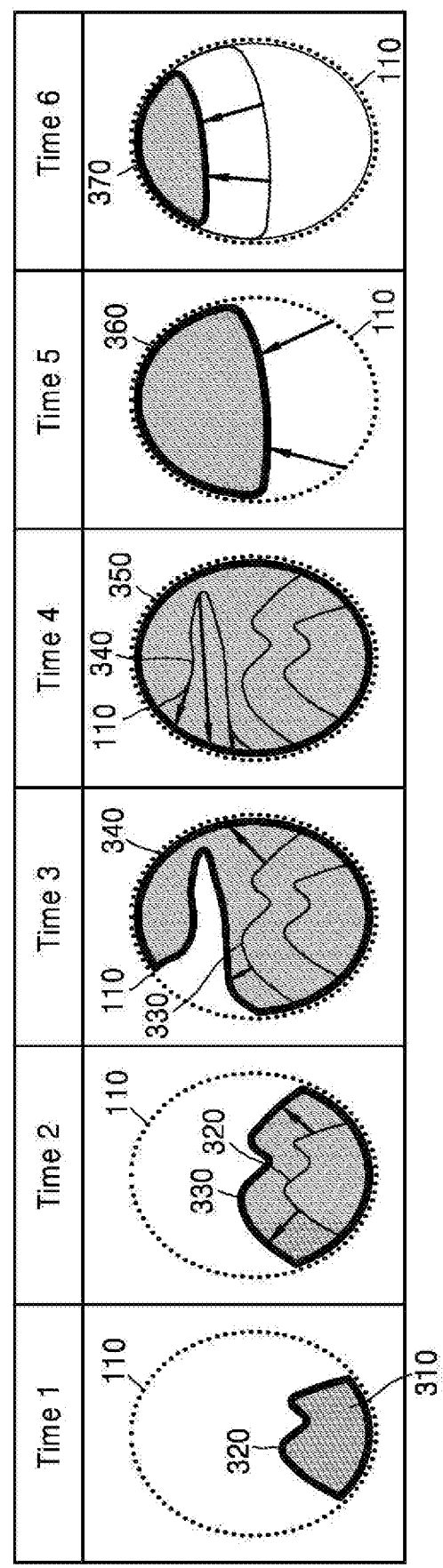
FIG. 3A is an example in which an ultrasound diagnosis apparatus determines a target tissue region based on a brightness value of an ROI, according to an exemplary embodiment.

FIG. 3A is an example in which the ultrasound diagnosis apparatus 1000 determines a target tissue region based on a brightness value of an ROI, according to an exemplary embodiment Referring to FIG. 3A, the ultrasound diagnosis apparatus 1000 may determine a target tissue region by expanding an ROI to a region having a brightness value whose difference from a brightness value of the ROI is less than or equal to a preset value.

After a contrast agent is introduced into an object, when a user input for capturing an image of a target tissue is received, the ultrasound diagnosis apparatus 1000 may acquire a plurality of ultrasound images of the target tissue with respect to time.

The ultrasound diagnosis apparatus 1000 may select an ultrasound image captured when time 1 has elapsed after introducing the contrast agent into the object and receive a user input for setting an ROI 320 in the selected ultrasound image.

On the ultrasound image captured when time 1 has elapsed after introducing the contrast agent into the object, only a portion 310 of a target tissue region 110 may appear bright while the rest of target tissue region 110 may appear dark.

Thus, the user may set the ROI 320 to include only the portion 310 that appears bright in the ultrasound image. Furthermore, according to an exemplary embodiment, the ROI 320 may be set by the ultrasound diagnosis apparatus 1000. For example, the ultrasound diagnosis apparatus 1000 may receive a user input for selecting a region in the ultrasound image and determine the ROI 320 by expanding the selected region to a region having a brightness whose difference from a brightness of the selected region is less than or equal to a preset value.

The ultrasound diagnosis apparatus 1000 may determine the set ROI 320 to be a portion of the target tissue region 110 into which the contrast agent is introduced and appearing bright.

As the ROI 320 is set in the ultrasound image corresponding to time 1, the ultrasound diagnosis apparatus 1000 may obtain an ultrasound image captured when time 2 has elapsed after introducing the contrast agent into the object and determine a region where the contrast agent spreads in the obtained ultrasound image.

The ultrasound diagnosis apparatus 1000 may expand the ROI 320 to a region 330 having a brightness value whose difference from a brightness value of the set ROI is less than or equal to a preset value. For example, the ultrasound diagnosis apparatus 1000 may calculate an average brightness value for the ROI 320 in the ultrasound image corresponding to time 1 and expand, in the ultrasound image corresponding to time 2, the ROI 320 to a region 330 whose difference from the calculated average brightness value of the ROI 320 is less than or equal to the preset value from among the surrounding regions of the ROI 320.

Since a user captures an image of a target tissue by hardly moving a probe in order to obtain a contrast image, as a contrast agent is introduced, only brightness values of a plurality of ultrasound images of the target tissue vary while objects such as organs or bones are represented by almost the same pixels in the plurality of ultrasound images. Furthermore, as the contrast agent flows into or out of the target tissue, a brightness value of a specific region may gradually increase or decrease. Based on these characteristics of a contrast image, the ultrasound diagnosis apparatus 1000 may expand the ROI 320 by using optical-flow based image processing techniques. Examples of the optical-flow image processing techniques may include, but are not limited to, a Lucas-Kanade algorithm and a camshaft algorithm.

For example, the ultrasound diagnosis apparatus 1000 may determine a position in an ultrasound image in a next frame, to which a pixel in the ROI 320 is moved, and expand the ROI 320 based on the determined position. For example, the ultrasound diagnosis apparatus 1000 may determine, based on a brightness value of a first pixel in an ultrasound image, pixels in a next frame having brightness values whose differences from the brightness value of the first pixel are less than or equal to a preset difference value from among pixels surrounding the first pixel, and expand the ROI 320 to an ROI 330 including the determined pixels.

Furthermore, the ultrasound diagnosis apparatus 1000 may expand the ROI 320 based on a shape of the set ROI 320. For example, if the set ROI 320 has an elliptical shape, the ultrasound diagnosis apparatus 1000 may determine an ROI in a next frame so that a shape of the ROI in the next frame does not deviate significantly from the elliptical shape. For example, if the set ROI 320 has an elliptical shape, and an ROI in a next frame determined based on a brightness value has an elliptical shape combining a straight line, the ultrasound diagnosis apparatus 1000 may exclude a region of the straight line combined with the elliptical shape from the ROI.

Furthermore, the ultrasound diagnosis apparatus 1000 may obtain an ultrasound image captured when time 3 has elapsed after introducing the contrast agent into the object and determine a region to which the contrast agent spreads in the obtained ultrasound image. For example, the ultrasound diagnosis apparatus 1000 may calculate an average brightness value of the ROI 330 in the ultrasound image corresponding to time 2 and expand, in the ultrasound image corresponding to time 3, the ROI 330 to a region 340 whose difference from the calculated average brightness value of the ROI 330 is less than or equal to a preset value from among the surrounding regions of the ROI 330.

Furthermore, the ultrasound diagnosis apparatus 1000 may obtain an ultrasound image captured when time 4 has elapsed after introducing the contrast agent into the object and determine an expanded ROI 350 in the obtained ultrasound image.

Furthermore, the ultrasound diagnosis apparatus 1000 may obtain an ultrasound image captured when time 5 has elapsed after introducing the contrast agent into the object and determine a region where residues of the contrast agent remain in the obtained ultrasound image. For example, the ultrasound diagnosis apparatus 1000 may calculate an average brightness value of the ROI 350 in the ultrasound image corresponding to time 4 and determine, in the ultrasound image corresponding to time 5, a region having a brightness value whose difference from the average brightness value of the ROI 350 is less than or equal to a preset value from among the surrounding regions of the ROI 350.

In this case, if the determined region has a size less than or equal to a preset size, the ultrasound diagnosis apparatus 1000 may reduce the ROI 350 to a region 360 having a brightness value whose difference from the average brightness value of the ROI 350 is less than or equal to a preset value from among regions inside the ROI 350.

Furthermore, if the determined region has a size less than or equal to the preset size, the ultrasound diagnosis apparatus 1000 may determine the ROI 350 determined in the ultrasound image corresponding to time 4 as a target tissue region.

Furthermore, the ultrasound diagnosis apparatus 1000 may calculate an average brightness value of the ROI 360 in the ultrasound image corresponding to time 5 and reduce, in the ultrasound image corresponding to time 6, the ROI 360 to a region 370 having a brightness value whose difference from the average brightness value of the ROI 360 is less than or equal to a preset value from among regions inside the ROI 360.

In this way, the ultrasound diagnosis apparatus 1000 may determine a target tissue region in the plurality of ultrasound images. Furthermore, the ultrasound diagnosis apparatus 1000 may determine the ultrasound image corresponding to time 4 as an ultrasound image captured when the contrast agent is introduced into the entire target tissue.

Figure 3B:
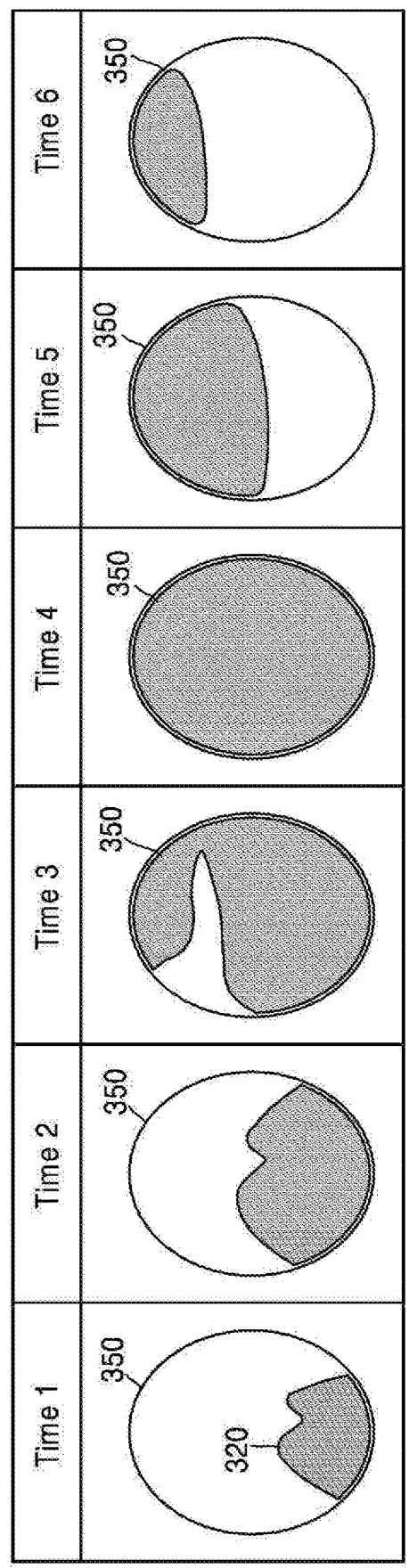
FIG. 3B is an example in which an ultrasound diagnosis apparatus calculates, based on a target tissue region determined by the ultrasound diagnosis apparatus, an average of brightness values of the determined target tissue region with respect to time, according to an exemplary embodiment.

FIG. 3B is an example in which an ultrasound diagnosis apparatus 1000 calculates, based on a target tissue region determined by the ultrasound diagnosis apparatus 1000, an average of brightness values of the determined target tissue region with respect to time, according to an exemplary embodiment Referring to FIG. 3B, the ultrasound diagnosis apparatus 1000 may calculate, based on a determined target tissue region described with reference to FIG. 3A, an average of brightness values of the target tissue region with respect to time. The ultrasound diagnosis apparatus 1000 may calculate an average of brightness values of a determined target tissue region with respect to time by applying the determined target tissue region to each of the obtained plurality of ultrasound images.

Figure 4:
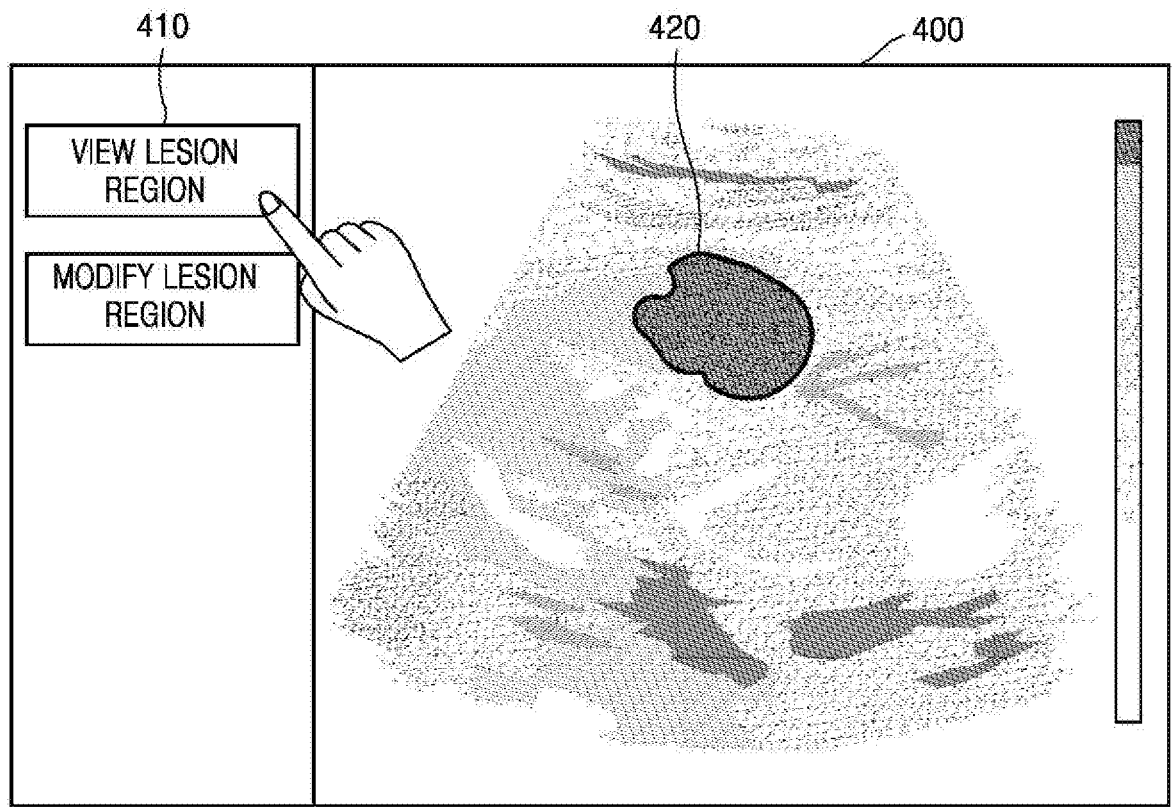
FIG. 4 illustrates an example in which an ultrasound diagnosis apparatus displays a target tissue region on an ultrasound image, according to an exemplary embodiment.

FIG. 4 illustrates an example in which the ultrasound diagnosis apparatus 1000 displays a target tissue region on an ultrasound image, according to an exemplary embodiment.

Referring to FIG. 4, when a user input is received, the ultrasound diagnosis apparatus 1000 may display a target tissue region on an ultrasound image.

For example, the ultrasound diagnosis apparatus 1000 may display a button 410 for displaying the target tissue region and receive a user input for selecting the button 410.

When the user input for selecting the button 410 is received, the ultrasound diagnosis apparatus 1000 may display an ultrasound image 400 showing the entire target tissue region and display a closed curve 420 on the target tissue region in the displayed ultrasound image 400. The target tissue region may be a region tracked by the ultrasound diagnosis apparatus 1000 based on an ROI set by the user, or a region set by the user.

Thus, the user may identify the target tissue region of which an average brightness value is calculated with respect to time.

Figure 5:
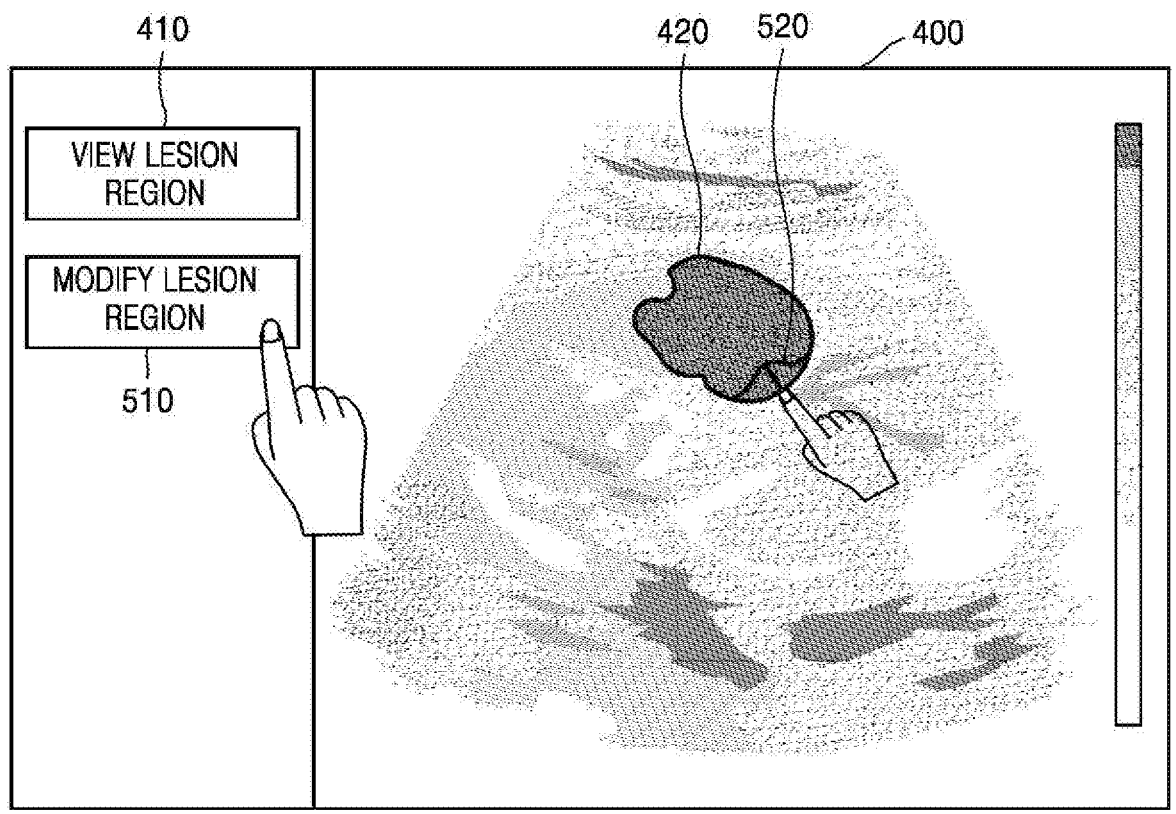
FIG. 5 illustrates an example in which an ultrasound diagnosis apparatus receives a user input for modifying a target tissue region according to an exemplary embodiment.

FIG. 5 illustrates an example in which the ultrasound diagnosis apparatus 1000 receives a user input for modifying a target tissue region according to an exemplary embodiment.

Referring to FIG. 5, the ultrasound diagnosis apparatus 1000 may display a target tissue region on an ultrasound image and receive a user input for modifying the displayed target tissue region.

For example, the ultrasound diagnosis apparatus 1000 may display a button 510 for modifying the target tissue region and receive a user input for selecting the button 510.

When the user input for selecting the button 510 is received, the ultrasound diagnosis apparatus 1000 may display an ultrasound image 400 showing the entire target tissue region and display a closed curve 420 on the target tissue region in the displayed ultrasound image 400. The target tissue region may be a region tracked by the ultrasound diagnosis apparatus 1000 based on an ROI set by the user, or a region set by the user.

Furthermore, the ultrasound diagnosis apparatus 1000 may receive a user input for modifying a shape or size of the closed curve 420. For example, the ultrasound diagnosis apparatus 1000 may select a region inside the closed curve 420 and receive a user input for moving the selected region. When the user input for moving the selected region is received, the ultrasound diagnosis apparatus 1000 may determine as a target tissue region a region inside a closed curve 520 obtained by adjusting a position of the selected region.

As the target tissue region changes, the ultrasound diagnosis apparatus 1000 may recalculate an average of brightness values of the changed target tissue region inside the closed curve 520 with respect to time. Furthermore, the ultrasound diagnosis apparatus 1000 may display a graph representing a change in an average of brightness values with respect to time.

Figure 6:
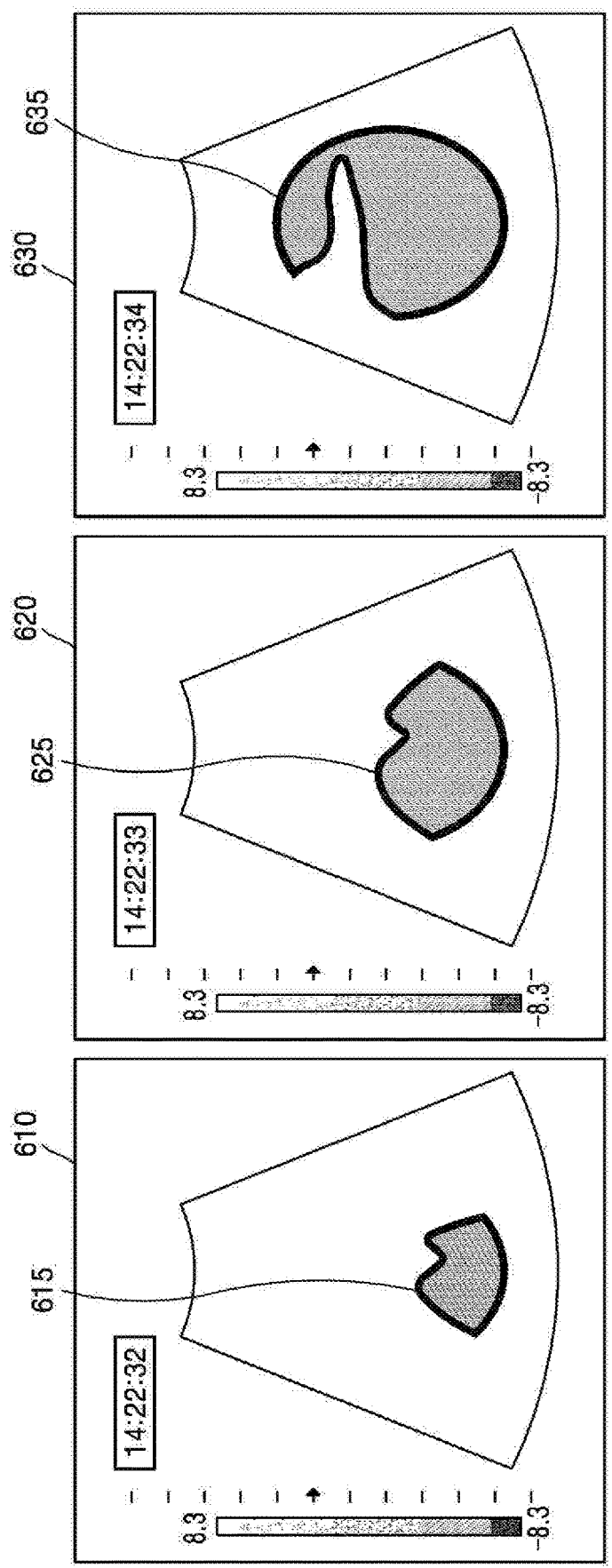
FIG. 6 illustrates an example in which an ultrasound diagnosis apparatus displays a target tissue region tracked by the ultrasound diagnosis apparatus on an ultrasound image, according to an exemplary embodiment.

FIG. 6 illustrates an example in which the ultrasound diagnosis apparatus 1000 displays a target tissue region tracked by the ultrasound diagnosis apparatus 1000 on an ultrasound image, according to an exemplary embodiment.

Referring to FIG. 6, the ultrasound diagnosis apparatus 1000 may display on a plurality of ultrasound images a target tissue region tracked in the ultrasound image.

The ultrasound diagnosis apparatus 1000 may display the plurality of ultrasound images sequentially. Furthermore, the ultrasound diagnosis apparatus 1000 may reproduce a moving image, including the plurality of ultrasound images, as a frame.

Furthermore, the ultrasound diagnosis apparatus 1000 may display a second ultrasound image 620 subsequent to the first ultrasound image 610 and a closed curve 625 representing a tracked target tissue region on an expanded ROI within the second ultrasound image 620. Furthermore, the ultrasound diagnosis apparatus 1000 may display a third ultrasound image 630 subsequent to the second ultrasound image 620 and a closed curve 635 representing a tracked target tissue region on an expanded ROI within the third ultrasound image 630.

Thus, the ultrasound diagnosis apparatus 1000 may show a target tissue region tracked by the ultrasound diagnosis apparatus 1000 on each of the plurality of ultrasound images.

Figure 7:
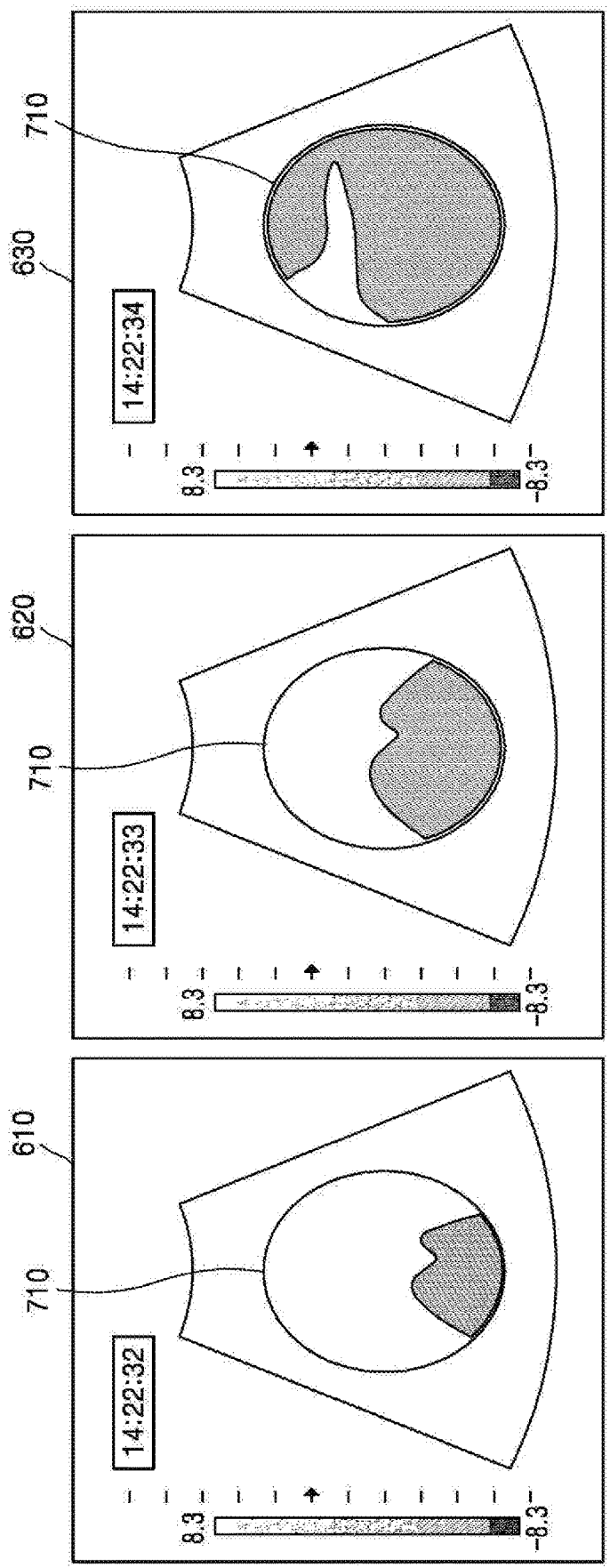
FIG. 7 illustrates an example in which an ultrasound diagnosis apparatus displays a determined target tissue region on an ultrasound image, according to an exemplary embodiment.

FIG. 7 illustrates an example in which the ultrasound diagnosis apparatus 1000 displays a determined target tissue region on an ultrasound image, according to an exemplary embodiment.

Referring to FIG. 7, the ultrasound diagnosis apparatus 1000 may display a previously determined target tissue region on a plurality of ultrasound images captured over time. The previously determined target tissue region may be determined by the ultrasound diagnosis apparatus 1000 based on an ROI set by the user, or may be set by the user.

The ultrasound diagnosis apparatus 1000 may display the plurality of ultrasound images sequentially. Furthermore, the ultrasound diagnosis apparatus 1000 may reproduce a moving image, including the plurality of ultrasound images, as a frame.

The ultrasound diagnosis apparatus 1000 may display a closed curve 710 representing a boundary of the previously determined target tissue region on the plurality of ultrasound images.

Thus, the user may identify a boundary of a target tissue while observing a change in the target tissue region into which a contrast agent is introduced FIG. 8 is a block diagram of the ultrasound diagnosis apparatus 1000 according to an exemplary embodiment.

Referring to FIG. 8, the ultrasound diagnosis apparatus 1000 according to the present exemplary embodiment may include a display 1400, a user input unit 1600, and a controller 1700.

However, all the components shown in FIG. 8 are not essential components. The ultrasound diagnosis apparatus 1000 may include more or fewer components than those shown in FIG. 8.

The display 1400 may display 2D and 3D ultrasound images. Furthermore, the display 1400 may display a user interface as well as a contrast image.

The user input unit 1600 may receive a user input. For example, the user input unit 1600 may receive a user input for setting an ROI in an ultrasound image.

The controller 1700 may control overall components of the ultrasound diagnosis apparatus 1000.

The controller 1700 may also determine a target tissue region in a contrast image. For example, the controller 1700 may determine, based on a set ROI, regions in a plurality of ultrasound images representing a tissue into which a contrast agent has been introduced, and determine a region having a maximum size from among the determined regions as a target tissue region.

Furthermore, the controller 1700 may calculate an average of brightness values of the determined target tissue region with respect to time.

Furthermore, the controller 1700 may determine regions representing a tissue into which a contrast agent has been introduced, based on at least one of a position and a brightness value of a set ROI.

Furthermore, the controller 1700 may determine the regions representing the tissue into which the contrast agent has been introduced by expanding the ROI to a region having a brightness value whose difference from the brightness value of the ROI is less than or equal to a preset value from among regions in a second ultrasound image subsequent to a first ultrasound image among a plurality of ultrasound images.

Furthermore, by taking into account a shape of the ROI set in the first ultrasound image, the ultrasound diagnosis apparatus 1000 may determine a region having a maximum size from among the regions in the plurality of ultrasound images representing the tissue into which the contrast agent has been introduced.

Furthermore, after displaying the first ultrasound image and setting the ROI in the first ultrasound image, the display 1400 may display the second ultrasound image and display an expanded ROI on the displayed second ultrasound image Thus, the ultrasound diagnosis apparatus 1000 may show expansion of the ROI as a size of a region representing a tissue into which the contrast agent has been introduced changes.

Furthermore, the display 1400 may display an ultrasound image showing a region having a maximum size from among a plurality of ultrasound images and display a target tissue region on the displayed ultrasound image.

Furthermore, the user input unit 1600 may receive a user input for adjusting the displayed target tissue region and recalculate brightness values of the adjusted target tissue region with respect to time based on the adjusted target tissue region.

Furthermore, the display 1400 may display a plurality of ultrasound images sequentially and display the determined target tissue region on the displayed plurality of ultrasound images.

Furthermore, the display 1400 may display a graph representing a calculated average brightness value of the target tissue region with respect to time.

Although FIG. 8 shows that the user input unit 1600 and the display 1400 are separate components, like a touch screen, the user input unit 1600 and the display 1400 may be implemented in an integrated form.

FIG. 9 is a block diagram of an ultrasound diagnosis apparatus 1000 according to another exemplary embodiment.

Unlike the ultrasound diagnosis apparatus 1000 of FIG. 8 including the display 1400, the user input unit 1600, and the controller 1700, the ultrasound diagnosis apparatus 1000 according to the present exemplary embodiment may further include a probe 20, an ultrasound transceiver 1100, an image processor 1200, a communication module 1300, and a memory 1500, which may be connected to one another via a bus 1800.

The ultrasound diagnosis apparatus 1000 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 1100 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 1000 by wire or wirelessly, and according to embodiments, the ultrasound diagnosis apparatus 1000 may include a plurality of probes 20.

A transmitter 1110 supplies a driving signal to the probe 20. The transmitter 110 includes a pulse generator 1112, a transmission delaying unit 1114, and a pulser 1116. The pulse generator 1112 generates pulses for forming transmission ultrasound waves based on a predetermined pulse repetition frequency (PRF), and the transmission delaying unit 1114 delays the pulses by delay times necessary for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 120 may include an amplifier 1122, an analog-to-digital converter (ADC) 1124, a reception delaying unit 1126, and a summing unit 1128. The amplifier 1122 amplifies echo signals in each channel, and the ADC 1124 performs analog-to-digital conversion with respect to the amplified echo signals. The reception delaying unit 1126 delays digital echo signals output by the ADC 1124 by delay times necessary for determining reception directionality, and the summing unit 1128 generates ultrasound data by summing the echo signals processed by the reception delaying unit 1126. In some embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 1212 extracts B mode components from ultrasound data and processes the B mode components. An image generator 1220 may generate an ultrasound image indicating signal intensities as brightness based on the extracted B mode components 1212.

Similarly, a Doppler processor 1214 may extract Doppler components from ultrasound data, and the image generator 1220 may generate a Doppler image indicating a movement of an object as colors or waveforms based on the extracted Doppler components.

According to an embodiment, the image generator 1220 may generate a three-dimensional (3D) ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

A display 1400 displays the generated ultrasound image. The display 1400 may display not only an ultrasound image, but also various pieces of information processed by the ultrasound diagnosis apparatus 1000 on a screen image via a graphical user interface (GUI). In addition, the ultrasound diagnosis apparatus 1000 may include two or more displays 1400 according to embodiments.

The communication module 1300 is connected to a network 30 by wire or wirelessly to communicate with an external device or a server. The communication module 1300 may exchange data with a hospital server or another medical apparatus in a hospital, which is connected thereto via a PACS. Furthermore, the communication module 1300 may perform data communication according to the digital imaging and communications in medicine (DICOM) standard.

The communication module 1300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 1300 may receive information about a diagnosis history or medical treatment schedule of a patient from a server and utilizes the received information to diagnose the patient. Furthermore, the communication module 1300 may perform data communication not only with a server or a medical apparatus in a hospital, but also with a portable terminal of a medical doctor or patient.

The communication module 1300 is connected to the network 30 by wire or wirelessly to exchange data with a server 32, a medical apparatus 34, or a portable terminal 36. The communication module 1300 may include one or more components for communication with external devices. For example, the communication module 1300 may include a local area communication module 1310, a wired communication module 1320, and a mobile communication module 1330.

The local area communication module 1310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 1320 refers to a module for communication using electric signals or optical signals. Examples of wired communication techniques according to an embodiment may include communication via a twisted pair cable, a coaxial cable, an optical fiber cable, and an Ethernet cable.

The mobile communication module 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various data processed by the ultrasound diagnosis apparatus 1000. For example, the memory 1500 may store medical data related to diagnosis of an object, such as ultrasound data and an ultrasound image that are input or output, and may also store algorithms or programs which are to be executed in the ultrasound diagnosis apparatus 1000.

The memory 1500 may be any of various storage media, e.g., a flash memory, a hard disk drive, EEPROM, etc. Furthermore, the ultrasound diagnosis apparatus 1000 may utilize web storage or a cloud server that performs the storage function of the memory 1500 online.

The user input unit 1600 refers to a means via which a user inputs data for controlling the ultrasound diagnosis apparatus 1000. The user input unit 1600 may include hardware components, such as a keypad, a mouse, a touch pad, a touch screen, and a jog switch. However, embodiments are not limited thereto, and the user input unit 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 1700 may control all operations of the ultrasound diagnosis apparatus 1000. In other words, the controller 1700 may control operations among the probe 20, the ultrasound transceiver 1100, the image processor 1200, the communication module 1300, the display 1400, the memory 1500, and the user input unit 1600 shown in FIG. 9.

All or some of the probe 20, the ultrasound transceiver 1100, the image processor 1200, the communication module 1300, the display 1400, the memory 1500, the user input unit 1600, and the controller 1700 may be implemented as software modules. Also, at least one of the ultrasound transmission/reception unit 1100, the image processor 1200, and the communication module 1300 may be included in the control unit 1700; however, the inventive concept is not limited thereto.

Exemplary embodiments may be implemented through non-transitory computer-readable recording media having recorded thereon computer-executable instructions such as program modules that are executed by a computer. The non-transitory computer-readable recording media may be any available media that can be accessed by a computer and include both volatile and nonvolatile media and both detachable and non-detachable media. Furthermore, the non-transitory computer-readable recording media may include computer storage media and communication media. The computer storage media include both volatile and nonvolatile and both detachable and non-detachable media implemented by any method or technique for storing information such as computer-readable instructions, data structures, program modules, or other data. The communication media typically embody computer-readable instructions, data structures, program modules, other data of a modulated data signal, or other transmission mechanism, and may include any information transmission media.

Furthermore, in the present specification, the term "unit" may be a hardware component such as a processor or circuit and/or a software component that is executed by a hardware component.

The above description is provided for illustration, and it will be understood by those of ordinary skill in the art that various changes in form and details may be made therein without departing from essential features and the spirit and scope of the present inventive concept as defined by the following claims. Accordingly, the above embodiments and all aspects thereof are examples only and are not limiting. For example, each component defined as an integrated component may be implemented in a distributed fashion. Likewise, components defined as separate components may be implemented in an integrated manner.

The scope of the present inventive concept is defined not by the detailed description thereof but by the appended claims, and all the changes or modifications within the scope of the appended claims and their equivalents will be construed as being included in the present inventive concept.

What is claimed is:

1. An ultrasound diagnosis apparatus comprising:
an image processor configured to generate, as an amount of a contrast agent introduced into a target tissue of an object changes, a plurality of ultrasound images of the target tissue with respect to time;

a display configured to display a first ultrasound image corresponding to a first time point from among the plurality of ultrasound images;

a controller configured to receive a user input for setting a region of interest (ROI) in the first ultrasound image;

determine, based on the set ROI, regions in the plurality of ultrasound images representing the target tissue into which the contrast agent has been introduced; and determine a region having a maximum size from among the determined regions as a target tissue region, wherein the controller determines the regions representing the target tissue into which the contrast agent has been introduced by calculating a brightness value of the set ROI in the first ultrasound image, and expanding the set ROI in the first ultrasound image to a region in a second ultrasound image having a second brightness value whose difference from the brightness value of the set ROI is less than or equal to a preset value, wherein the second ultrasound image corresponds to a second time point from among the plurality of ultrasound images, and the second time point is subsequent to the first time point, and wherein the display displays the plurality of ultrasound images sequentially and displays the determined regions representing the tissue into which the contrast agent has been introduced together with a closed curve representing a boundary of the determined target tissue region on the displayed plurality of ultrasound image.

2. The ultrasound diagnosis apparatus of claim 1, wherein the controller calculates an average of brightness values of the determined target tissue region.

3. The ultrasound diagnosis apparatus of claim 2, wherein the display displays a graph representing the calculated average of brightness values of the target tissue region.

4. The ultrasound diagnosis apparatus of claim 1, wherein the controller determines the regions representing the tissue into which the contrast agent has been introduced, based on a position and the brightness value of the set ROI.

5. The ultrasound diagnosis apparatus of claim 1, wherein the display displays the second ultrasound image subsequently to the first ultrasound image and shows expansion of the ROI as a size of a region representing the tissue into which the contrast agent has been introduced changes by displaying the expanded ROI on the displayed second ultrasound image.

6. The ultrasound diagnosis apparatus of claim 1, wherein the controller determines the region having the maximum size from among the regions in the plurality of ultrasound images representing the tissue into which the contrast agent has been introduced by taking into account a shape of the set ROI in the first ultrasound image.

7. The ultrasound diagnosis apparatus of claim 1, wherein the display displays an ultrasound image showing the region having the maximum size from among the plurality of ultrasound images and displays the target tissue region on the displayed ultrasound image.

8. The ultrasound diagnosis apparatus of claim 7, wherein the controller receives a user input for adjusting the displayed target tissue region, and recalculates, based on the adjusted target tissue region, an average of brightness values of the adjusted target tissue region with respect to time.

9. A method of acquiring information based on a contrast image, the method comprising:

generating, as an amount of a contrast agent introduced into a target tissue of an object changes, a plurality of ultrasound images of the target tissue with respect to time;

displaying a first ultrasound image corresponding to a first time point from among the plurality of ultrasound images;

receiving a user input for setting a region of interest (ROI) in the first ultrasound image;

determining, based on the set ROI, regions in the plurality of ultrasound images representing the target tissue into which the contrast agent has been introduced;

determining a region having a maximum size from among the determined regions as a target tissue region;

displaying the determined regions representing the tissue into which the contrast agent has been introduced together with a closed curve representing a boundary of the determined target tissue region on the displayed plurality of ultrasound images, wherein the determining of the regions in the plurality of ultrasound images representing the tissue into which the contrast agent has been introduced based on the set ROI comprises determining the regions representing the tissue into which the contrast agent has been introduced by calculating a brightness value of the set ROI in the first ultrasound image and expanding the set ROI in the first ultrasound image to a region in a second ultrasound image having a second brightness value whose difference from the brightness value of the set ROI is less than or equal to a preset value, wherein the second ultrasound image corresponds to a second time point from among regions in a second ultrasound image, and the second time point is subsequent to the first time point.

10. The method of claim 9, further comprising calculating an average of brightness values of the determined target tissue region.

11. The method of claim 10, further comprising displaying a graph representing the calculated average of brightness values of the target tissue region.

12. The method of claim 9, wherein the determining of the regions in the plurality of ultrasound images representing the tissue into which the contrast agent has been introduced based on the set ROI comprises determining the regions representing the tissue into which the contrast agent has been introduced, based on a position and the brightness value of the set ROI.

13. The method of claim 9, further comprising:

displaying the second ultrasound image subsequently to the first ultrasound image; and showing expansion of the ROI as a size of a region representing the tissue into which the contrast agent has been introduced changes by displaying the expanded ROI on the displayed second ultrasound image.

14. The method of claim 9, wherein the determining of the regions in the plurality of ultrasound images representing the tissue into which the contrast agent has been introduced based on the set ROI comprises determining the region having the maximum size from among the regions in the plurality of ultrasound images representing the tissue into which the contrast agent has been introduced by taking into account a shape of the set ROI in the first ultrasound image.

15. The method of claim 9, further comprising:
displaying an ultrasound image showing the region having the maximum size from among the plurality of ultrasound images; and
displaying the target tissue region on the displayed ultrasound image.

16. The method of claim 15, further comprising:
receiving a user input for adjusting the displayed target tissue region; and
recalculating, based on the adjusted target tissue region, an average of brightness values of the adjusted target tissue region with respect to time.

\* \* \* \* \*